United States Patent

Suzuki et al.

[11] Patent Number: 5,912,344
[45] Date of Patent: Jun. 15, 1999

[54] CHEMILUMINESCENT GROUP-CONTAINING CARBODIIMIDE COMPOUND

[75] Inventors: Osamu Suzuki; Gen Masuda; Namiko Shiohata; Kazuko Matsumoto, all of Tokyo, Japan

[73] Assignee: Nisshinbo Industries, Inc., Tokyo, Japan

[21] Appl. No.: 08/858,127

[22] Filed: May 19, 1997

[30] Foreign Application Priority Data

Jun. 11, 1996 [JP] Japan .................................. 8-149553

[51] Int. Cl.⁶ .................................................. C07D 413/12
[52] U.S. Cl. ........................................ 544/126; 530/391.9
[58] Field of Search .......................... 530/391.9; 544/126

[56] References Cited

U.S. PATENT DOCUMENTS 4,895,955  1/1990  Ford et al. .............................. 548/303

FOREIGN PATENT DOCUMENTS 0718 300 A1  6/1996  European Pat. Off. .

OTHER PUBLICATIONS

Chemical Abstracts, vol. 124, No. 15, Apr. 9, 1996.
Yamamoto (Abstract), JP 06 271581, Sep. 27, 1994.
Beilstein Registry No. 1826311, vol. 11, 1975.

Takana et al, Chem. Abs. 118, No. 229734, (1993). Weeks et al, Chem. Abs. 105, 127528 (1986) Serono Symp. Pub. Raven Press (1986), 30 (Mab) 41–8.

*Primary Examiner*—Ponnathapura Achutamurthy
*Assistant Examiner*—T. D. Wessendorf
*Attorney, Agent, or Firm*—Jones & Askew, LLP

[57] ABSTRACT

Using the chemiluminescent group-containing carbodiimide compound represented by the following formula or its quaternary ammonium salt as the label in the nucleic acid detection method or immunoassay, labeling can be made efficiently for a short time, a nucleic acid derived from nature can be labelled, and highly sensitive assay is enabled.

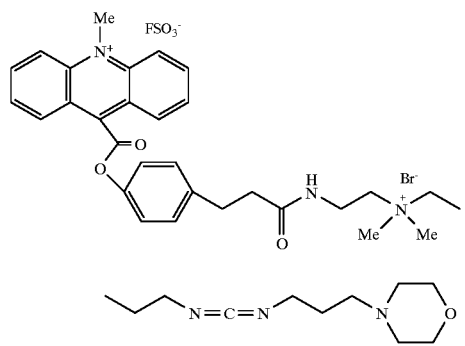

1 Claim, No Drawings

CHEMILUMINESCENT GROUP-CONTAINING CARBODIIMIDE COMPOUND

FIELD OF THE INVENTION

The present invention relates to a novel chemiluminescent group-containing carbodiimide compound. More specifically, the present invention relates to a novel chemiluminescent group-containing carbodiimide compound which is an assay reagent having high sensitivity and capable of labeling easily, a process for producing it, and a nucleic acid detection method or immunoassay using it.

BACKGROUND OF THE INVENTION

In various biological analyses, assay methods for detecting a target substance using a specific detectable label have been developed so far. For example, in the nucleic acid detection method by hybridization using the labelled nucleic acid, a nucleic acid (DNA or RNA) to be used as a probe is labelled and brought into contact with a sample containing a nucleic acid to be detected under conditions that hybrid can be formed. If the sample contains a nucleic acid having a base sequence complementary to that of the nucleic acid used as a probe, this nucleic acid binds (hybridize) to the probe to form a nucleic acid-nucleic acid hybrid. The target nucleic acid can be detected by measuring the label contained in the hybrid. In the immunoassay using labelled antigen or a labelled antibody, when an antigen is to be detected, it can be detected by labeling an antibody which is specifically bound to the antigen, effecting formation of an antigen-antibody complex, and detecting the label contained in the complex.

As the label to be used in such nucleic acid detection methods and immunoassay, radioactive substances, non-radioactive substances such as biotin or digoxigenin compounds, fluorescent substances, chemiluminescent substances, and the like are exemplified. Among these, chemiluminescent substances have been expected to be useful as the label because of its high detection sensitivity.

The known method of labeling using a chemiluminescent substance is, for example, a method which comprises reacting a nucleic acid bound to an amino linker with a chemiluminescent substance having a group reactive with an amino group to label the nucleic acid with the chemiluminescent substance (Clinical Chemistry, Vol. 35, No. 8, p.1588–1594, 1989).

However, this method requires to prepare an amino linker-bound nucleic acid, which makes the operation complicated. Further, the method has a disadvantage in that a nucleic acid derived from nature cannot be labelled by directly binding it to a chemiluminescent substance.

SUMMARY OF THE INVENTION

An object of the present invention is to provide a novel chemiluminescent group-containing carbodiimide compound to be used as a label in a nucleic acid detection method or immunoassay, which enables efficient labeling for a short period of time, can be used to label a nucleic acid derived from nature, and has high sensitivity.

It is known that a carbodiimide compound reacts with an nucleic acid. For example, it is reported that a carbodiimide compound reacts with guanine and thymine which is not forming hydrogen bond in a nucleic acid, to form an addition product [P. T. Gilham, J. Amer. Chem. Soc., 84, 688 (1962)].

As a result of intensive investigation of a method of simply and efficiently introducing a chemiluminescent group into a nucleic acid or a protein, the present inventors found that the above problems can be solved by introducing a chemiluminescent moiety to a carbodiimide compound utilizing high reactivity of a carbodiimide moiety with a nucleic acid, a protein and the like, to thereby achieve the present invention. The present invention provides a chemiluminescent group-containing carbodiimide compound represented by the following formula (I):

$$B-N=C=N-L-CL \qquad (I)$$

wherein B represents a monovalent organic group which binds to a carbodiimide group; CL represents a chemiluminescent group; and L represents a linker which connects the carbodiimide group with the chemiluminescent group.

The present invention also provides a process for producing the above-described chemiluminescent group-containing carbodiimide compound which comprises a step of reacting a carbodiimide group-containing compound represented by the formula (IV):

$$B-N=C=N-(CH_2)_p-NR'_2 \qquad (IV)$$

wherein B has the same definition as in the above formula (I); R' represents a straight-chain or branched alkyl group having from 1 to 6 carbon atoms; and p represents an integer of from 1 to 12, with a halogen-containing chemiluminescent compound represented by the formula (V):

$$CL-X \qquad (V)$$

wherein CL has the same definition as in the above formula (I); and X represents a halogen atom.

Further, the present invention relates to a method for detecting a nucleic acid by hybridization using a labelled nucleic acid, characterized in that the above-described chemiluminescent group-containing carbodiimide compound is used as the label.

Furthermore, the present invention relates to a method for immunoassay using a labelled antigen or a labelled antibody, characterized in that the above-described chemiluminescent group-containing carbodiimide compound is used as the label.

The chemiluminescent group-containing carbodiimide compound represented by the formula (I) according to the present invention is a compound having a carbodiimide group which is highly reactive with a nucleic acid base, and a chemiluminescent moiety which has highly sensitive detection reactivity. It is useful as a label used in a nucleic acid detection method, immunoassay or the like.

DETAILED DESCRIPTION OF THE INVENTION

The embodiments of the present invention will be described below.

(1) Chemiluminescent group-containing carbodiimide compound of the invention

The chemiluminescent group-containing carbodiimide compound of the present invention has a structure represented by the formula (I). Any of such a compound can be used as long as it has the structure in which a chemiluminescent moiety (CL) is bound to a carbodiimide group via a linker (L). Among these carbodiimide compounds, compounds represented by the following formula (II) are preferably used.

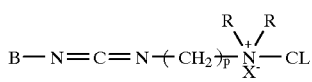

(II)

wherein R represents a hydrogen atom or a straight-chain or branched alkyl group having from 1 to 6 carbon atoms; X represents a halogen atom; p represents an integer of from 1 to 12; and B and CL have the same definition as in the above formula (I).

In the above formula (II), the chemiluminescent group CL is not particularly limited as long as it is induced from chemiluminescent substances. Such chemiluminescent substances can be selected from various chemiluminescent substances which can be detected by the known methods, for example, an acridinium derivative, a luminol derivative, an isoluminol derivative, a dioxetane derivative, and the like. Alternatively, compounds which can be easily converted into chemiluminescent compounds though they are not chemiluminescent by nature, can be also used.

Among examples, chemiluminescent groups selected from those represented by the following formula (CL) are particularly preferable. In the formula, Me represents a methyl group, $FSO_3^-$ represents a fluorosulfonate ion (hereinafter the same definition shall be applied).

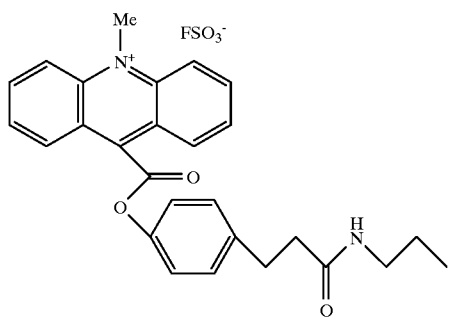

(CL)

In the formula (II), B is not particularly limited as long as it is a monovalent organic group, and preferably represents an organic group selected from those represented by the following formula (B), a tertiary amino group, such as a dimethylamino group and diethylamino group, or a quaternary ammonium group thereof. In the formula (B), k represents an integer of from 1 to 12, preferably 3 to 6.

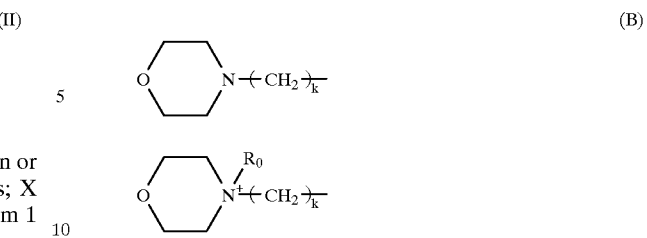

(B)

wherein k represents an integer of from 1 to 12. $R_0$ represents an organic group.

Examples of the carbodiimide compound of the present invention includes compounds represented by the following formula (III) or their quaternary ammonium salt.

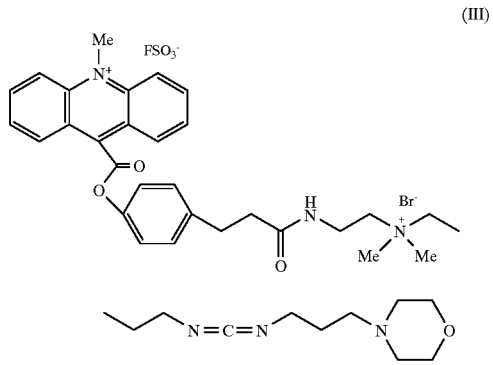

(III)

Examples of the quaternary ammonium salt of the compound represented by the formula (III) include compounds represented by the following formula (III'). In the formula (III'), TsO⁻ represents a p-toluenesulfonate ion.

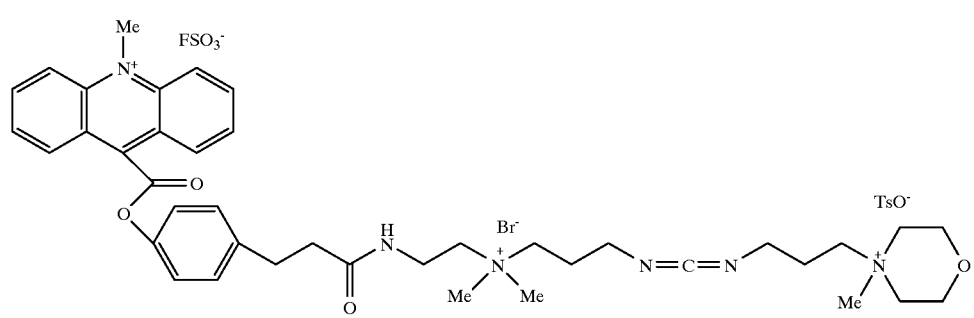

(III')

(2) Process for producing the chemiluminescent group-containing carbodiimide compound of the present invention The chemiluminescent group-containing carbodiimide compound of the present invention represented by the formula (I) can be produced by a process comprising a step of reacting the carbodiimide group-containing compound represented by the formula (IV) with the halogen-containing chemiluminescent compound represented by the formula (V). Namely, the carbodiimide group-containing compound represented by the formula (IV) have an alkylamino group at its end which reacts with a terminal halogen atom (X) of the halogen-containing chemiluminescent compound represented by the formula (V) to form a linker (L in the formula (I)). This reaction is shown in the following reaction formula.

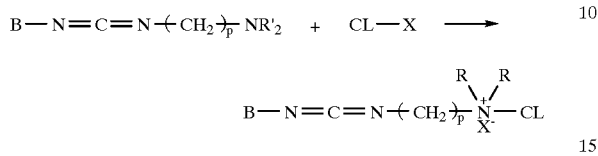

The carbodiimide group-containing compound represented by the formula (IV) and the halogen-containing chemiluminescent compound represented by the formula (V) can be appropriately selected depending on the structure of the desired chemiluminescent group-containing carbodiimide compound. Examples of the carbodiimide group-containing compound represented by the formula (IV) includes N-(3-dimethylamino)propyl-N'-(3-morpholino)-propylcarbodiimide, 1-ethyl-3,3-dimethylaminopropylcarbodiimide, bis-(3,3-dimethylaminopropyl)carbodiimide, and the like. Such carbodiimide group-containing compounds can be obtained as shown in the reaction formula below by reacting a dialkylamino group-containing isothiocyanate compound ((a) in the reaction formula) with alkylamine (b) to synthesize a thiourea compound (c), and subjecting the resulting thiourea compound to desulfulization using mercury oxide or lead oxide as a catalyst.

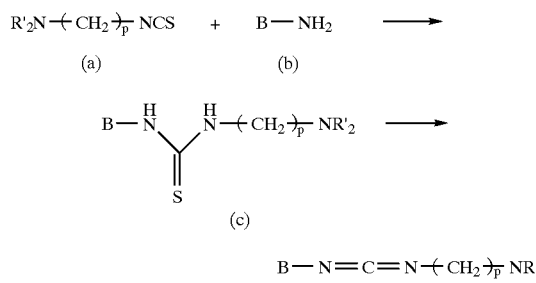

The dialkylamino group-containing isothiocyanate compounds and the alkylamines used in this reaction can be appropriately selected depending on the structure of the desired carbodiimide group-containing compound. Examples of the dialkylamino group-containing isothiocyanate compound includes 3-dimethylaminopropylisothiocyanate, 3-(4-morpholino)propylisothiocyanate, and the like. Examples of the alkylamines include N-(3-aminopropyl)morpholine, N,N-dimethylpropanediamine, and the like.

Examples of the halogen-containing chemiluminescent compound represented by the formula (V) includes bromide, iodide, chloride, or the like of an acridinium ester represented by the formula (V').

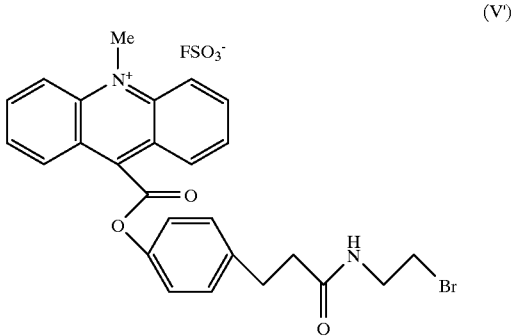

These halogen-containing chemiluminescent compounds can be obtained by reacting various chemiluminescent compound which is detectable by the known method with a halogenating reagent such as 2-bromoethylamine, 2-iodoethylamine, 2-chloroethylamine, and the like. Examples of such chemiluminescent compounds include chemiluminescent substance ester derivatives such as succinimide ester derivatives or p-nitrophenol derivatives of acridinium represented by the following formula (V").

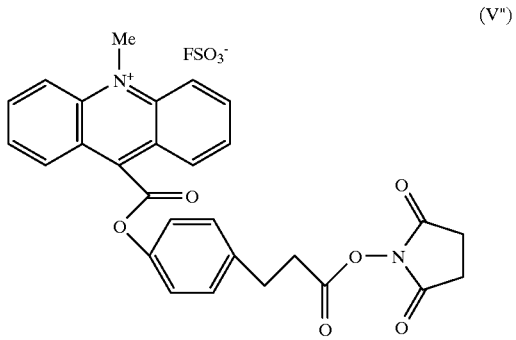

Each of these reaction steps can be carried out by the known methods using commonly used solvent(s) such as dimethylformamide (DMF), acetone, methylene chloride, and the like.

In the present invention, a desired chemiluminescent group-containing carbodiimide compound can be obtained by reacting the carbodiimide group-containing compound represented by the formula (IV) with the halogen-containing chemiluminescent compound represented by the formula (V) using commonly used solvent(s) such as dimethylformamide, methylene chloride, and the like.

The thus-obtained chemiluminescent group-containing carbodiimide compound can be converted into a desired quaternary ammonium salt by reacting it with methyl p-toluenesulfonate (TsOMe), methyl iodide, ethyl iodide, dimethyl sulfate, or the like in a solvent such as dimethylformamide.

The chemiluminescent group-containing carbodiimide compound of the present invention obtained by the above methods can be suitably used as the label in a nucleic acid detection method and immunoassay. In this case, the chemiluminescent group-containing carbodiimide compound of the present invention can be brought into contact with a nucleic acid such as DNA or a protein such as antigen or antibody to be labelled by mixing these compounds in a solvent to bind to each other. Namely, a chemiluminescent substance, which is a highly sensitive detection reagent, can be attached as the label to a substance to be labelled including a nucleic acid or a protein by binding the carbodiimide group, which is highly reactive with a nucleic acid base, of the chemiluminescent group-containing carbodiimide compound of the present invention to the nucleic acid or the protein. In case of binding the chemiluminescent group-containing carbodiimide compound of the present invention to a nucleic acid or a protein, the carbodiimide group is preferably contacted under its reactive condition, for example, under alkaline conditions such as about pH 7.5 to 8.5.

(3) Nucleic acid detection method of the invention

The chemiluminescent group-containing carbodiimide compound of the present invention can be used as the label in the nucleic acid detection method by hybridization using a labelled nucleic acid. Namely, the nucleic acid labelled with the chemiluminescent group-containing carbodiimide compound can be used as a probe for hybridization. The nucleic acid to be assayed can be detected by allowing the nucleic acid to hybridize with the probe to form a nucleic acid-nucleic acid hybrid, removing free probe from the system, and detecting the label contained in the hybrid. In the present invention, the chemiluminescent group-containing carbodiimide compound used as the label can be detected by measuring chemiluminescence intensity and the like, using a chemiluminescence measuring apparatus, a photocounter, and so on. The nucleic acid to be assayed is usually immobilized on a membrane such as nylon membrane and nitrocellulose, prior to measure.

For hybridization in the nucleic acid detection method according to the present invention, any common nucleic acid hybridization method can be used, including colony hybridization, plaque hybridization, dot blot hybridization, Southern hybridization, Northern hybridization, and the like, except for using the chemiluminescent group-containing carbodiimide compound as the label for a nucleic acid probe. The nucleic acid to be assayed may be either DNA or RNA. The nucleic acid used as a probe may also be either DNA or RNA.

Labeling of a nucleic acid used as a probe can be preferably carried out by binding the label to polynucleotide or oligonucleotide using the above method. Alternatively, labelled nucleotide can be incorporated into polynucleotide or oligonucleotide by the polymerase reaction.

(4) Immunoassay of the invention

The above-described chemiluminescent group-containing carbodiimide compound of the present invention can be used as the label in immunoassay using a labelled antigen or a labelled antibody.

When an antigen is to be assayed, it can be detected by labeling an antibody which is specifically bound to the antigen, forming an antigen-antibody complex, then removing free antibody from the system, and detecting the label contained in the complex. In the present invention, the chemiluminescent group-containing carbodiimide compound to be used as the label can be detected by measuring chemiluminescence intensity and the like, using a chemiluminescence measuring apparatus, a photocounter, and so on. Alternatively, a first antibody which is specifically bound to the antigen is immobilized and allowed to bind to the antigen, then a labelled second antibody which is specifically bound to the antigen is further allowed to bind thereto. In this case, the first antibody and the second antibody may be the same polyclonal antibody, or different monoclonal antibodies. Further, one of them may be polyclonal antibody, and the other may be monoclonal antibody. In each case, alternatively, an unlabelled antibody may be used in place of a labelled antibody, an antigen is allowed to bind thereto, and a labelled second antibody which is specifically bound to the antibody is further allowed to bind thereto. Immunoglobulin derived from an animal which is used in preparing an antibody can be used to immunize a different animal to obtain the second antibody.

When an antibody is to be assayed, it can be detected by labeling an antigen which is specifically bound to the antibody, forming an antigen-antibody complex, then removing free antigen from the system, and detecting the label contained in the complex. When an antibody which is specifically bound to the antibody to be assayed can be obtained, it may be labelled and used to form an antibody-antibody complex.

Any commonly used procedure of immunoassay can be applied to the immunoassay of the present invention, except for using the chemiluminescent group-containing carbodiimide compound as the label for an antigen or an antibody. Immobilization of an antigen or an antibody, antigen-antibody reaction, washing procedure, and the like can be carried out in the same manner as in the commonly used methods. Any method of immunoassay including the direct method, the indirect method, the competitive method, and the like can be applied.

EXAMPLE

In the following, examples of the present Invention are described.

EXAMPLE 1

A chemiluminescent group-containing carbodiimide compound of the present invention was synthesized in the following manner. The reaction formulae will be illustrated in the respective steps.

(1) Synthesis of thiourea compound (Reaction formula (1))

In 15 ml of dry methylene chloride was dissolved 1.4 g (10 mmol) of 3-(dimethylaminopropyl)isothiocyanate and the mixture was cooled in ice. After adding 1.4 g (10 mmol) of N-(3-aminopropyl)morpholine, the mixture was stirred overnight at room temperature. Water was added to the reaction mixture and subjected to extraction with methylene chloride (5 ml×3 times). After dried over anhydrous potassium carbonate, the resulting mixture was concentrated to obtain 2.7 g (yield: 98%) of N-(3-dimethylamino)propyl-N'-(3-morpholino)propylthiourea (Compound-1 in the following Reaction formula (1). The same shall apply hereinafter).

REACTION FORMULA (1)

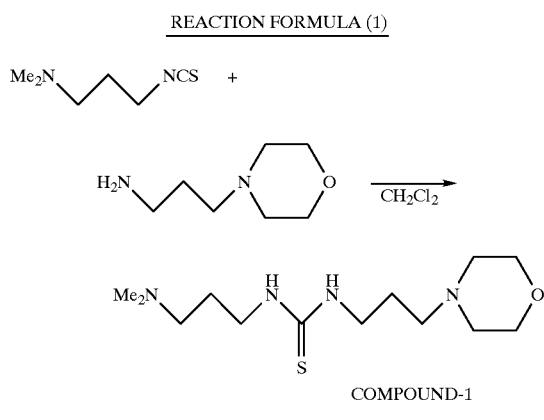

COMPOUND-1

(2) Synthesis of carbodiimide group-containing compound (Reaction formula (2))

In 35 ml of acetone was dissolved 2.7 g (10 mmol) of N-(3-dimethylamino)propyl-N'-(3-morpholino) propylthiourea (Compound-1). Further, 4.2 g (20 mmol) of mercury oxide was added thereto, and the resulting mixture was stirred for 2 hours under reflux. Then, the reaction mixture was allowed to cool and filtered. The solvent was distilled off to obtain a crude product. This product was evaporated under reduced pressure to obtain 1.5 g (yield: 60%) of N-(3-dimethylamino)propyl-N'-(3-morpholino) propylcarbodiimide (Compound-2). Its boiling point (b.p.) was from 125 to 128° C./0.2 mmHg.

REACTION FORMULA (2)

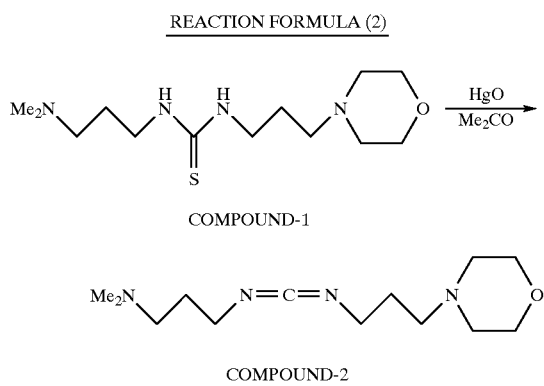

(3) Synthesis of chemiluminescent substance bromide (Reaction formula (3))

40 mg (0.085 mmol) of succinimide ester derivative of acridinium (Compound-3) was dissolved in 1 ml of 1:1 mixture of 1N sodium borate buffer and methanol. After adding 18 mg (0.09 mmol) of 2-bromoethylamine hydrochloride to the mixture, reaction was carried out for 18 hours. Then, the reaction mixture was subjected to high performance liquid chromatography (HPLC). The column used was Puracil C-18 (tradename, Waters). Gradient elution using water : methanol of from 60:40 to 40:60 was applied and detection was made at ultraviolet absorption of 380 nm. The peak at 12 minutes was collected and the collected fraction was lyophilized to obtain 27 mg of acridinium ester bromide (Compound-4).

REACTION FORMULA (3)

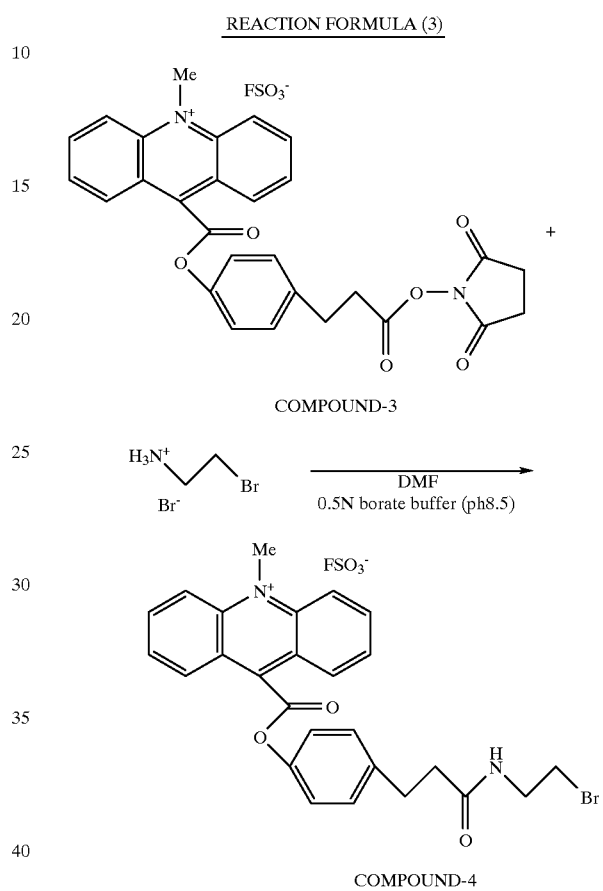

(4) Synthesis of chemiluminescent group-containing carbodiimide compound (Reaction formura (4)).

In 3 ml of dimethylformamide was dissolved 27 mg (0.05 mmol) of the acridinium ester bromide (Compound-4). Then, 2 ml of dimethylformamide solution of 12 mg (0.05 mmol) of N-(3-dimethylamino)propyl-N'-(3-morpholino) propylcarbodiimide (Compound-2) was added thereto and stirred at room temperature for 18 hours. After the solvent was distilled off under reduced pressure, the remaining reaction mixture was dissolved in a small amount of dimethylformamide and added dropwise to dimethyl ether. Yellow crystals precipitated were collected by filtration, and dried to obtain 20 mg of an acridinium ester group-containing carbodiimide compound (Compound-5).

REACTION FORMULA (4)

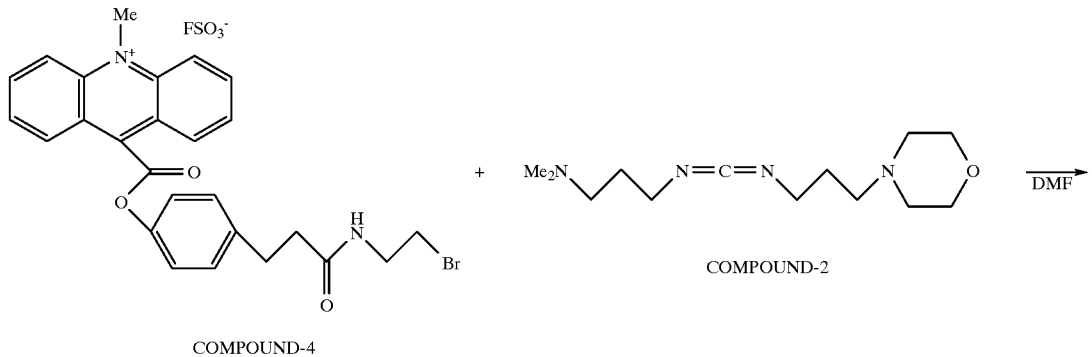

COMPOUND-4 + COMPOUND-2 →(DMF)

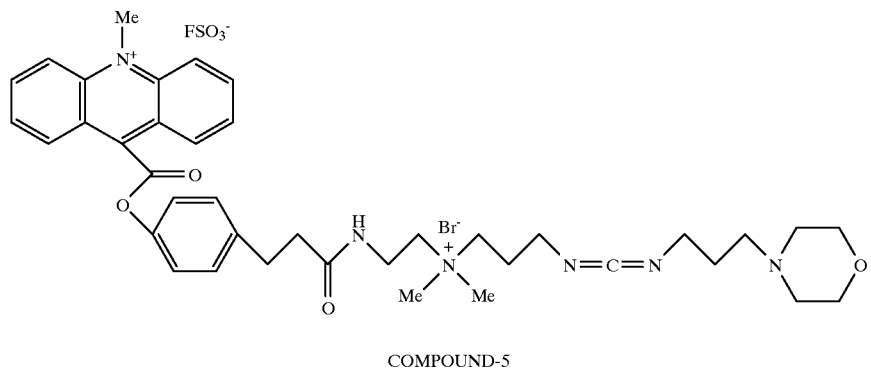

COMPOUND-5

(5) Synthesis of quaternary ammonium salt of chemiluminescent group-containing carbodiimide compound (Reaction formula (5))

In 3 ml of dimethylformamide was dissolved 20 mg (0.025 mmol) of the acridinium ester group-containing carbodiimide compound (Compound-5). Then, 2 ml of dimethylformamide solution of 5 mg (0.025 mmol) of methyl p-toluenesulfonate (TsOMe) was added thereto and stirred at room temperature for 18 hours. After the solvent was distilled off under reduced pressure, the remaining reaction mixture was dissolved in a small amount of dimethylformamide and added dropwise to dimethyl ether. White crystals precipitated were collected by filtration, and dried to obtain 13 mg of a quaternary ammonium salt of the acridinium ester group-containing carbodiimide compound (Compound-6).

REACTION FORMULA (5)

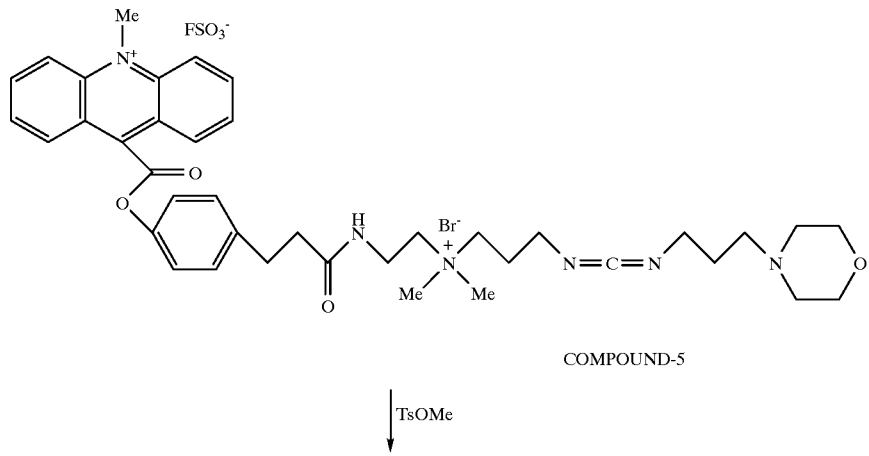

COMPOUND-5

↓ TsOMe

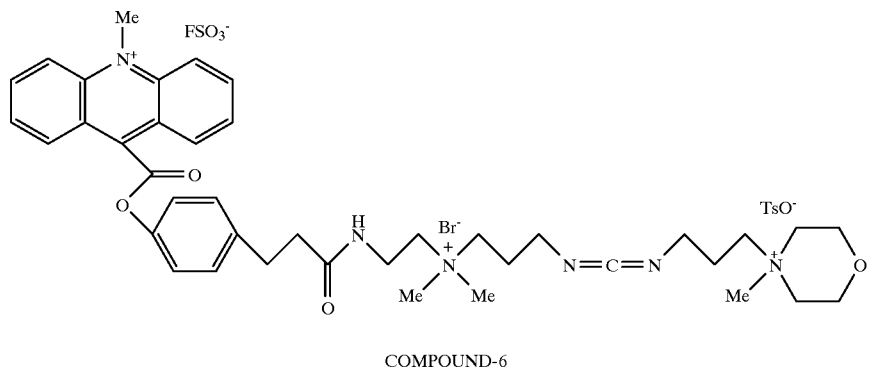

COMPOUND-6

EXAMPLE 2

Using Compound-6 synthesized in Example 1, a chemiluminescence-labelled DNA was prepared by introducing a chemiluminescent group into DNA in the following manner.

The reaction mixture (phage DNA (replicative form of M13mp18: Takara Shuzo) 1 μg; 0.1 M borate buffer (pH 8.5); 0.25% SDS; and 0.1 M quaternary ammonium salt of the acridinium ester group-containing carbodiimide (Compound-6)) was incubated at 85° C. for 1 minute. Then, in order to remove the unreacted chemiluminescent group-containing carbodiimide compound (Compound-6), the reaction mixture was mixed with 3 M sodium acetate in a 1/9 amount of the sample and cold ethanol in a double amount of the sample, and the resulting mixture was allowed to stand at −80° C. for 45 minutes. The mixture was centrifuged at 4° C. at 12,000 rpm for 15 minutes using a centrifuge (H-1500FR Model, Kokusansha) to remove the upper layer. Then, 500 μl of 70% ethanol was added to the residue, and centrifugation was further carried out at 4° C. at 12,000 rpm for 1 minute and 30 seconds. After removing the upper layer, the precipitate was dissolved in 100 μl of sterilized water, the DNA concentration was measured with a UV detector (UV-VISIBLE RECORDING SPECTROPHOTOMETER UV-2100, Shimadzu) and the mixture was kept at −20° C.

EXAMPLE 3

Using the chemiluminescence-labelled DNA obtained in Example 2, DNA detection was carried out in the following manner.

Dilutions of phage DNA (replicative form DNA of M13mp18, Takara Shuzo) was prepared so as to give 100 pg/ml–0.1 pg/ml. The dilutions were heat-treated at 100° C. for 10 minutes to heat-denature the DNA and immobilized by adsorption on the 96-well microtiter plate. After washing, 100 μl of a solution for prehybridization [5×SSC (1×SSC= 0.15 M NaCl, 0.015 M sodium citrate), 5×Denhardt's solution (0.02% BSA), 25 mM sodium phosphate buffer (pH 6.6), 50% formamide, and 0.5 mg/ml denatured salmon sperm DNA] was added to each well, followed by incubation at 60° C. for 2 hours. Then, a 100 μl portion of a hybridization solution was [5×SSC, 1×Denhardt's solution, 25 mM sodium phosphate buffer (ph 6.6), 45% formamide, 0.2 mg/ml denatured salmon sperm DNA, and 10 ng/ml chemiluminescence-labelled DNA probe prepared in Example 2] was added to each well, followed by incubation overnight at 42° C. After removing the supernatant from the reaction mixture, 0.2×SSC and 0.1% SDS kept at 50° C. were added thereto and incubated (washed) for 5 minutes. This operation was repeated five times.

Each well of the microtiter plate was separated and set in a chemiluminescence measuring apparatus (Luminescence reader BLR-301, Aloka). Then, 120 μl of 0.5% hydrogen peroxide/0.1 N nitric acid solution was added thereto. Further, 120 μl of 0.125% cethyltrimethylammonium chloride/0.25 N sodium hydroxide solution was added thereto, then chemiluminescence generated from it was measured for 2 seconds. As a result, 0.1 pg/ml of unlabelled DNA was detected.

EXAMPLE 4

Using the chemiluminescent group-containing carbodiimide compound of the present invention as the label, a chemiluminescence-labelled protein was prepared in the following manner.

The reaction mixture [anti-rabbit IgG antibody (goat) (Anti-RABBIT IgG (goat), VECTOR LABORATORIES) 100 μg; 0.1 M borate buffer (ph 9.0); and 0.1 M the chemiluminescent group-containing carbodiimide compound (Compound-6 obtained in Example 1)] was allowed to stand on ice for 10 minutes. Then, 10% SDS was added thereto so as to give a concentration of 0.3% based on the total amount and the mixture was centrifuged at 5,000 rpm for 15 minutes using microtube for centrifugation (Ultrafree C3LGC, tradename: Millipore) to remove unreacted carbodiimide compound. Then, 50 μl each of 100 mM sodium phosphate buffer (pH 7.6) and 50 mM NaCl was added to a filter cup to centrifuge at 5,000 rpm for 10 minutes. After repeating the same procedure, the residue was transferred to an Eppendorf tube and 100 mM sodium phosphate buffer (pH 7.6) and 50 mM NaCl were added thereto to give a 0.1 M solution. The resulting solution was kept at 4° C.

EXAMPLE 5

Serial dilutions of the chemiluminescence-labelled protein prepared in Example 4 were prepared and a 10 μl portion each of them was pipetted into vials for the chemiluminescence measuring apparatus (Luminescence reader BLR-301, Aloka). The vials were set in the chemiluminescence measuring apparatus and 300 μl of 0.5% hydrogen peroxide/0.1 N nitric acid solution was added thereto. Further, 300 μl of 0.125% cethyltrimethylammonium chloride/0.25 N sodium hydroxide solution was added thereto, then chemiluminescence generated from it was measured for 2 seconds. As a result, 0.1 pg/ml of chemiluminescence-labelled anti-rabbit IgG antibody (goat) was detected.

The use of the chemiluminescent group-containing carbodiimide compound of the present invention enables highly sensitive nucleic acid detection or immunoassay with simple operation.

What is claimed is:

1. A chemiluminescent group-containing carbodiimide compound represented by the formula (III) or its quarternary ammonium salt:

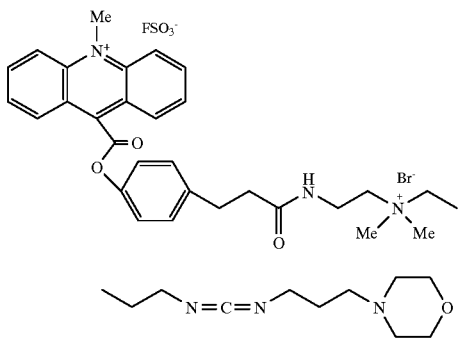

(III)

wherein Me represents a methyl group.

* * * * *